United States Patent [19]

Lhonore et al.

[11] 4,313,010

[45] Jan. 26, 1982

[54] PROCESS FOR MAKING NITROPARAFFINS BY NITRATION OF ETHANE IN THE GASEOUS PHASE

[75] Inventors: Pierre Lhonore; Bernard Jacquinot, both of Douai; Jacques Quibel, Maisons Laffitte; Roger Mari, Villers les Nancy, all of France

[73] Assignee: Societe Chimique de la Grande Paroisse, Azote et Produits Chimiques, Paris, France

[21] Appl. No.: 94,153

[22] Filed: Nov. 14, 1979

[30] Foreign Application Priority Data

Nov. 14, 1978 [FR] France ............................ 78 32118

[51] Int. Cl.³ .................. C07C 76/02; C07C 79/04
[52] U.S. Cl. .................................. 568/948; 568/947
[58] Field of Search .......................... 568/947, 948

[56] References Cited

U.S. PATENT DOCUMENTS

| | | | |
|---|---|---|---|
| 2,071,122 | 2/1937 | Haas et al. | 568/947 |
| 2,332,491 | 10/1943 | Senkus | 568/947 |
| 2,512,587 | 6/1950 | Stengel | 568/947 |
| 2,609,401 | 9/1952 | Haas et al. | 568/947 |
| 2,883,432 | 4/1959 | Spaeth | 568/947 |
| 2,883,433 | 4/1959 | Spaeth | 568/947 |
| 2,883,434 | 4/1959 | Spaeth | 568/947 |
| 3,272,874 | 9/1966 | Abbott | 568/947 |
| 3,378,596 | 4/1968 | Toops, Jr. et al. | 568/948 |
| 3,780,115 | 12/1973 | Lhonore et al. | 568/947 |
| 4,260,838 | 4/1981 | Lhonore et al. | 568/947 |

FOREIGN PATENT DOCUMENTS

| | | | |
|---|---|---|---|
| 1069133 | 11/1959 | Fed. Rep. of Germany | 568/947 |
| 1439414 | 12/1966 | France | 568/947 |
| 2158681 | 6/1973 | France | 568/947 |
| 2199753 | 4/1974 | France | 568/947 |

OTHER PUBLICATIONS

Albright, L. F., "Nitration of Parafins", Chem. Eng., vol. 73, No. 12, pp. 149–156 (Jun. 1966).

*Primary Examiner*—Teddy S. Gron
*Attorney, Agent, or Firm*—Browdy and Neimark

[57] ABSTRACT

Nitroparaffins are made in the homogeneous gaseous phase by nitration of ethane, performed in the presence of an active agent carrying an NO or $NO_2$ group that is easily transferable. The process is applicable particularly to making nitromethane with high yields.

7 Claims, No Drawings

PROCESS FOR MAKING NITROPARAFFINS BY NITRATION OF ETHANE IN THE GASEOUS PHASE

FIELD OF THE INVENTION

This invention relates to making nitroparaffins in the homogeneous gaseous phase by nitration of ethane.

BACKGROUND OF THE INVENTION

Various industrial processes for nitration of saturated hydrocarbons, particularly propane, have already been proposed. Nitration of propane, particularly by nitrogen peroxide, under pressure, leads to an orientation of the final products towards nitropropanes with a very clear predominance of 2-nitropropane. However, this product does not at present constitute the more usable nitroparaffin either in its use as a nitroparaffin or the derivatives that it makes possible for one to obtain.

One of the present industrial problems resides in the search for means making it possible to obtain in nitration operations a spectrum of products suited to market demands and therefore to achieve an industrial manufacturing unit having sufficient operational flexibility to meet these requirements. Further, use of less expensive materials more available in large amounts is also a considerable industrial objective. Use of ethane has appeared to provide a solution to these two problems.

However, nitration of ethane by standard nitration agents—nitric acid and nitrogen peroxide—makes it possible to obtain nitromethane and nitroethane only in proportions of 30% nitromethane and 70% nitroethane, which does not correspond to the needs of the market. Research on nitration of ethane was conducted at the Purdue Research Foundation in Indiana. Study was done on nitration of ethane at atmospheric pressure by a nitrating agent such as nitric acid or nitrogen peroxide (U.S. Pat. No. 2,071,122 and H. J. Hibshman et al, Industrial and Engineering Chemistry, vol. 32, No. 3, pp. 427-9). These laboratory tests conducted forty years ago and possibly in the interim do not seem to have led to an industrial embodiment not only because of the lack of correspondence between the products manufactured and user demands, but also because the more difficult recovery of ethane cannot be performed under the same conditions as for propane without greater energy consumption, because of the very high molar ratio $C_2H_6/NO_2$.

SUMMARY OF INVENTION

This invention has for an object a process of industrial production of nitroparaffins from ethane in the presence of an oxidizing agent with yields of conversion to nitromethane higher than those obtained experimentally and resulting in high nitromethane contents that can reach 98%.

According to this process, the quantitative ratios of the various ingredients of the reaction mixture, the reaction contact time, the reaction temperature and pressure are selected and controlled so that nitration is done in a homogeneous phase, and as a function of the spectrum of nitroparaffins desired. The temperature and pressure at which the nitration is performed are selected so that the totality of the reaction mixture: hydrocarbon, oxygenated gas, nitrating agent and other possible ingredients, are used in the homogeneous gaseous phase. The ratios of the ingredients of the reaction mixture, the contact time and temperature are parameters that make it possible to cause the spectrum of nitroparaffins produced to vary.

DETAILED DESCRIPTION OF EMBODIMENTS

The nitrating agent is nitrogen peroxide or nitric acid, used alone or in mixture. The oxidizing agent is a gas containing oxygen, such as air, superoxygenated air or pure oxygen.

It has been found that the spectrum of nitroparaffins produced in nitration of ethane can be largely modified by addition during nitration of a certain number of active products. It is advantageous to perform nitration in the presence of an active agent carrying an NO or $NO_2$ group, easily transferable, such as 2-nitropropane and nitroethane, introduced alone or in mixture.

The active agent that participates in the reaction can be added at such a rate that the molar ratio of active agent to nitrating agent is at most equal to 3 and is adjusted as a function of the desired spectrum of nitroparaffins. Variations of this ratio give a great flexibility in adapting the installation to market demand. And this ratio is adjusted as a function of the desired modification of the nitroparaffin spectrum. The active agent, alone or in mixture, can advantageously be a recycling product from the nitration reaction.

The desired results are obtained by selecting a molar ratio of ethane/nitrating agent between 12 and 2.5, preferably between 8 and 3; an ethane/oxygen ratio between 12 and 45, preferably 15 to 40.

The reaction contact time is a function of the temperature and pressure, between 0.1 and 20 seconds and preferably between 1 and 20 seconds. The nitration pressure is kept between 1 and 27 bars and preferably between 5 and 15 bars. The reaction temperatures are, when nitrogen peroxide is used as the nitrating agent, between 250° and 450° C., preferably between 270° and 400° C.; when nitric acid is used, between 340° and 600° C., preferably between 420° and 520° C.

On the other hand, it has been noted that performance of nitration of ethane in the presence of one or more gases which are inert in the reaction and to the reacted products, facilitates recovery of residual ethane coming from the nitration. This possibility of nitration is advantageous if the volumetric proportion of inert gases does not exceed 50%, and it is preferably kept between 7 and 30% of the total volume subjected to nitration. The gas that is inert to the totality of the reaction ingredients and nitroparaffins produced, introduced alone or in mixture, can be selected from nitrogen, carbon monoxide, carbon dioxide, hydrogen, methane, argon.

It is also advantageous to preheat the reactants at a controlled temperature at most equal to nitration temperature. This preheating is performed separately for the oxidizing and nitrating agents, on the one hand, and the ethane, on the other. The recycling gas and the active agent can be preheated indifferently either with the ethane or with the oxidizing and nitrating agents.

The final reaction mixing, made at a temperature at most equal to the nitration temperature, should be performed with particular care. The oxidizing and nitrating agents are introduced in the ethane stream possibly containing an inert gas. This mixing should occur at a point as close as possible to the reaction zone, in which the temperature should be rigorously controlled by suitable means that particularly allows a good heat transfer.

Examples that illustrate the invention in a nonlimiting manner are given below.

EXAMPLE 1

Nitration of ethane is performed at temperatures varying from 342° to 351° C. under a pressure of 10 bars, in the presence of air, the nitrating agent being nitrogen peroxide, for a contact time of 5.8 to 7.1 seconds, the ethane/nitrogen peroxide molar ratios in moles varying from 3.9 to 6.42 at the reactor input, ethane/oxygen molar ratios under the same conditions of 22 to 35 moles. Nitration is performed in the presence of inert gas (I), made up of carbon monoxide (test 4), carbon dioxide (test 3), a mixture of the carbon oxides (test 1) and nitrogen (test 2).

The test results are given in table I below, in which the reaction temperatures T° C. are in degrees centigrade, the reaction times TS are expressed in seconds, the pressure P in bars, nitrogen peroxide and ethane are represented respectively by $NO_2$ and $C_2H_6$, $NO_2$ c and $C_2H_6$ c represent consumption by weight of each, the nitroparaffins produced are designated by weight as NPf, nitromethane by $NC_1$, nitroethane by $NC_2$, and —nitropropane by $2NC_3$, and the inert gases are designated by I. The composition of the effluent is expressed in percentage by weight of nitroparaffins and consumption by weight of ethane $C_2H_6$ c and nitrogen peroxide $NO_2$ c reduced to kilogram of the totality of nitroparaffins produced NPf.

TABLE I

| Test No | 1 | 2 | 3 | 4 |
|---|---|---|---|---|
| T °C. | 351 | 342 | 344 | 345 |
| TS Seconds | 7.1 | 5.9 | 5.8 | 6 |
| P bar | 10 | 10 | 10 | 10 |
| $C_2H_6/NO_2$ mol. | 5.68 | 6.42 | 3.9 | 6.4 |
| $C_2H_6/O_2$ mol. | 35 | 22 | 27 | 30 |
| I Inert gases | CO + $CO_2$ | $N_2$ | $CO_2$ | CO |
| I/$C_2H_6$ mol. | CO:0.33 $CO_2$:0.34 | 0.17 | 0.31 | 0.61 |
| Composition NP | | | | |
| 2 $NC_3$ % | 7 | | | |
| N $C_1$ % | 35 | 30 | 31 | 30 |
| N $C_2$ % | 58 | 70 | 69 | 70 |
| $C_2H_6$ c / NPf | 4.98 | 1.89 | 0.73 | 1.88 |
| $NO_2$ c / NPf | 3.17 | 1.48 | 1.18 | 1.33 |

EXAMPLE 2

Nitration of ethane is performed at temperatures varying from 326° to 353° C., at a pressure of 10 bars, in the presence of air, the nitrating agent being nitrogen peroxide, during a contact time varying from 6 to 7.2 seconds, the ethane/nitrogen peroxide molar ratios carrying from 3.8 to 7.92 moles and ethane/oxygen ratio under the same conditions being 21.7 to 35 moles. Nitration was performed in the presence of an active agent: (A-A): recycling 2-nitropropane $2NC_3$ or nitroethane $NC_2$ and in the presence of inert gas.

The test results are given in table II.

The specific consumption of active agent recycled (AAR) or (introduced) represents the difference between the mass of the same constituent collected at the reactor output. It is expressed in kg of the recycled material per kg of nitroparaffins produced NPf. In all cases where the nitration reaction was performed with recycling or introduction of an active agent, for determining the composition of this material in the liquids produced, only the difference between the mass of this collected compound and the mass of the same active compound introduced at the reactor input was considered.

TABLE II

| Test No | 5 | 6 | 7 | 8 | 9 | 10 |
|---|---|---|---|---|---|---|
| T °C. | 345 | 342 | 350 | 353 | 326 | 25,1 |
| TS | 7.2 | 7.1 | 7 | 6.1 | 6 | 6 |
| P bar | 10 | 10 | 10 | 10 | 10 | 10 |
| $C_2H_6/NO_2$ mol. | 5.7 | 5.7 | 5.7 | 7.92 | 3.8 | 3.8 |
| $C_2H_6/O_2$ mol. | 35 | 35 | 35 | 21,7 | 25,1 | 25.1 |
| Inert gases | $CO_2$ | CO | CO + $CO_2$ | $N_2$ | $CO_2$ | $CO_2$ |
| I/$C_2H_6$ mol. | 0.64 | 0.67 | CO:0.33 $CO_2$:0.34 | 0.17 | 0.31 | 0.31 |
| Recycling | 2 $NC_3$ | 2 $NC_3$ | 2 $NC_3$ | $NC_2$ | $NC_2$ | $NC_2$ |
| AA/$NO_2$ mol. | 0.13 | 0.15 | 0.16 | 0.17 | 0.12 | 0.11 |
| Composition NP | | | | | | |
| $NC_1$ % | 37.4 | 35.4 | 37.6 | 59 | 49.3 | 98 |
| $NC_2$ % | 62.6 | 64.6 | 62.4 | 38 | 50.7 | 2 |
| 2 NC 3 % | | | | 3 | | |
| $C_2H_6$ c / NPf | 1.97 | 1.60 | 4.92 | 1.80 | 1.47 | 3.66 |
| N $O_2$ c / NPf | 1.88 | 1.44 | 3.17 | 3.21 | 1.90 | 1.16 |
| AAR c / NPf | 0.55 | 0.72 | 0.79 | | | 0.19 |

EXAMPLE 3

Nitration of ethane is performed at temperatures of 338° to 341° C., under a pressure of 10 bars, in the presence of air, the nitrating agent being nitrogen peroxide, for a contact time of 6 to 6.1 seconds, the molar ratios $C_2H_6/NO_2$ mol. being 7.54 and 7.77 and the molar ratios $C_2H_6/O_2$ mol being 21 and 22. Nitration was performed in the presence of recycling nitroethane $NC_2R$, in the absence of an inert gas.

The results are given in table III below.

| Test No | 11 | 12 |
|---|---|---|
| T °C. | 341 | 338 |
| ts | 6.1 | 6 |
| P bar | 10 | 10 |
| $C_2H_6/NO_2$ mol. | 7.54 | 7.77 |
| $C_2H_6/O_2$ mol. | 21 | 22 |
| N $C_2R/NO_2$ mol. | 0.20 | 0.15 |
| Composition NP | | |
| N $C_1$ % | 46 | 88 |
| N $C_2$ % | 51 | 9 |
| 2 N $C_3$ % | 3 | 3 |
| $C_2H_6$ c/NP f | 1.08 | 2.16 |
| $NO_2$ c/NP f | 2.11 | 1.26 |

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A process for making nitroparaffins with a high nitromethane content, comprising nitrating ethane with nitrogen peroxide in the presence of an oxidizing agent and further in the presence of an active agent selected from the group consisting of 2-nitropropane, nitroethane and a mixture thereof, with an active agent/nitrogen peroxide molar ratio in an amount sufficient to cause the reaction to become oriented toward increased nitromethane production, said ratio not exceeding 3, wherein the quantitative ratios of the reactants, the reaction contact time and the reaction temperature and pressure are so selected and controlled that the nitration is performed in a homogeneous phase as a function of the desired spectrum of nitroparaffins and within the following ranges:

ethane/nitrogen peroxide molar ratio: 12-2.5
ethane/oxidizing agent molar ratio: 12-45
reaction contact time: 0.1-20 seconds
reaction pressure: 1-27 bars
reaction temperature: 250°-450° C.

2. Process for making nitroparaffins, according to claim 1, wherein the active agent is a product of recycling from the reaction.

3. Process for making nitroparaffins according to claim 1 wherein the nitration reaction is performed in the presence of a gas inert to the reaction ingredients and nitroparaffins produced, introduced in a volumetric proportion not exceeding 50% of the total volume subjected to nitration.

4. Process for making nitroparaffins, according to claim 1, wherein the ethane/nitrogen peroxide molar ratio is between 8 and 3, the ethane/oxidizing agent molar ratio is between 15 and 40, the reaction contact time is between 1 and 10 seconds, the reaction pressure between 5 and 15 bars, and the reaction temperature between 270° and 400° C.

5. Process for making nitroparaffins, according to claim 3, wherein the inert gas is selected from the group consisting of nitrogen, carbon monoxide, carbon dioxide, hydrogen, methane, argon and any mixture of these gases, introduced in a volumetric proportion representing 7 to 30% of the total volume subjected to nitration.

6. Process for making nitroparaffins, according to claim 1, wherein said oxidizing agent is oxygen.

7. Process for making nitroparaffins, according to claim 6, wherein the reagents are preheated at a controlled temperature between 250° and 450° C.; the oxygen and nitrogen peroxide being preheated separately from the ethane; the active agent being preheated indiscriminately either with the ethane or with the oxygen and nitrogen peroxide at a temperature between 250° C. and 450° C.; and wherein the mixing is performed at a temperature at least equal to the reaction temperature, between 250° and 450° C., at a point as close as possible to the reaction zone; the oxygen and nitrogen peroxide being introduced in the ethane current.

* * * * *